(12) United States Patent
Chen et al.

(10) Patent No.: US 11,541,084 B2
(45) Date of Patent: Jan. 3, 2023

(54) METHOD OF PROMOTING BONE REGROWTH

(71) Applicant: GENMONT BIOTECH INC., Tainan (TW)

(72) Inventors: Yi-Hsing Chen, Tainan (TW); Wan-Hua Tsai, Kaohsiung (TW); Chia-Hsuan Chou, Tainan (TW); Chi Chien Lin, Taichung (TW)

(73) Assignee: .GENMONT BIOTECH INC, Tainan (TW)

( * ) Notice: Subject to any disclaimer, the term of this patent is extended or adjusted under 35 U.S.C. 154(b) by 332 days.

(21) Appl. No.: 16/983,335

(22) Filed: Aug. 3, 2020

(65) Prior Publication Data

US 2020/0368298 A1 Nov. 26, 2020

Related U.S. Application Data

(63) Continuation of application No. 15/603,487, filed on May 24, 2017, now abandoned.

(30) Foreign Application Priority Data

Feb. 20, 2017 (TW) ................. 106105625

(51) Int. Cl.
*A61K 35/747* (2015.01)
*A23L 33/135* (2016.01)
*C12N 1/20* (2006.01)
*C12R 1/25* (2006.01)

(52) U.S. Cl.
CPC .......... *A61K 35/747* (2013.01); *A23L 33/135* (2016.08); *C12N 1/20* (2013.01); *C12N 1/205* (2021.05); *A23V 2002/00* (2013.01); *A23Y 2220/67* (2013.01); *C12R 2001/25* (2021.05)

(58) Field of Classification Search
CPC ....... A61K 35/747; A23L 33/135; C12N 1/20; C12N 1/205; A23V 2002/00; A23Y 2220/67; C12R 2001/25
See application file for complete search history.

(56) References Cited

U.S. PATENT DOCUMENTS 6,511,685 B1   1/2003   Weissmahr
2017/0360854 A1  12/2017  Alenfall et al.

FOREIGN PATENT DOCUMENTS

| CN | 1300187 A | 6/2001 |
|---|---|---|
| CN | 101252943 A | 8/2008 |
| CN | 103037882 A | 4/2013 |
| CN | 104839664 A | 8/2015 |
| JP | 2003009814 A | 1/2003 |
| JP | 2017048244 A | 3/2017 |
| KR | 20160112699 A | 9/2016 |

OTHER PUBLICATIONS

Ohlsson et al., "Probiotics Protect Mice from Ovariectomy-Induced Cortical Bone Loss", PLoS ONE, Mar. 2014, vol. 9, Issue 3, e92368, 8 pages. (Year: 2014).*
Chiang et al., "Effect of bioactive compounds in Lactobacilli-fermented soy skim milk on femoral bone microstructure of aging mice", Journal of Science of Food and Agriculture, 2012, vol. 92, Issue 2, pp. 328-335. (Year: 2012).*
Chiang et al., "Antiosteoporotic Effects of Lactobacillus-Fermented Soy Skim Milk on Bone Mineral Density and the Microstructure of Femoral Bone in Ovariectomized Mice", Journal of Agricultural and Food Chemistry, 2011, vol. 59, pp. 7734-7742. (Year: 2011).*
Wang Fang , Ren Han-qiang , Shen Xiao-bo, "Effect of insul in combined alendronate sodium on bone mineral density and levels of serum".
Zhao Yu-mei, Liu Ting ,Li Jie, Chen De-cai "Changes of bone turnover markers in postmenopansal women with T2DM and osteoporosis".

* cited by examiner

*Primary Examiner* — Neil P Hammell
*Assistant Examiner* — Deepa Mishra
(74) *Attorney, Agent, or Firm* — Soroker Agmon Nordman

(57) ABSTRACT

A composition having *Lactobacillus Plantarum* strain GMNL-662 for promoting bone regrowth is provided. The *Lactobacillus Plantarum* strain GMNL-662 has an ability to promote the expression of osteogenic genes, inhibit the expression of osteoclast related genes, and promote the expression of osteogenesis-related cytokine TGF-β, so that the bone loss is improved.

4 Claims, 3 Drawing Sheets

Specification includes a Sequence Listing.

METHOD OF PROMOTING BONE REGROWTH

CROSS REFERENCE TO RELATED APPLICATIONS

This application claims the benefit of the filing date of Taiwan patent application No. 106105625, filed on Feb. 20, 2017, the disclosure of which is incorporated herein by reference.

FIELD OF THE INVENTION

The present invention relates to a composition including *Lactobacillus Plantarum* strain GMNL-662 for promoting bone regrowth, and in particular relates to a composition including *Lactobacillus Plantarum* strain GMNL-662 which has an ability of increasing the expression of osteogenic genes.

BACKGROUND OF THE INVENTION

Osteoporosis is a kind of systemic skeletal disease, which includes bone loss and bone tissue microstructure deterioration, resulting in bone fragility and risk of fracture.

During bone remodeling process, the bone formation of osteoblasts and bone resorption of osteoclast maintain the dynamic balance of bone tissue together. Once the bone resorption is over bone formation, bone loss will caused, and finally result in osteoporosis. In general, osteoporosis can be divided into postmenopausal osteoporosis and senile osteoporosis. Postmenopausal osteoporosis is common in women after menopause, due to the rapid reduction of estrogen in the female body, so that the osteoclast activity is increased to absorb the trabecular bone, and ultimately make the trabecular bone thinning, broken off, and make the number of the bone cells reduced or discontinuous, resulting in reduction of bone strength. Senile osteoporosis is caused by the decline of osteogenic cell function, insufficient calcium and vitamin D intake, intestinal absorption dysfunction, leading to reduced bone synthesis, thick loose cortical bone, and trabecular bone disappeared, so that bone strength is significantly reduced.

According to its mechanism, the current drugs for prevention and treatment of osteoporosis and fracture can be divided into anti-osteoclast or anti-loss drugs, bone formation or promoting osteoblast drugs, and mixed type drugs. Anti-osteoclast drugs include calcium, vitamin D, calcitonin, bisphosphonates, estrogen receptor modulators, sex hormones, osteoclast enzyme inhibitors, RANKL monoclonal antibody. The mixed type drug is currently strontium salt only. The drugs that control osteoporosis are accompanied by some side effects. It is found in the clinical trials that the use of drugs in combination has no addition effect, but will resist each other, or increase the incidence or strength of the side effects. Therefore, the current guidelines for various prevention and treatment of osteoporosis are not recommended to use two anti-loss reagents, or use one anti-loss reagent together with one promoting osteoblast reagent.

The osteoporotic drugs clinically used in the elderly and menopausal women, such as Fosamax, Tevanate, Covaxin (bisphosphonates drugs), will cause serious necrosis of jaw bone joint if users do not pay attention to oral hygiene, or the users are subject to tooth extraction, dental implant surgery. Recent studies have also found that it may cause the adverse reactions including atypical femoral fracture.

Although some literatures state that certain specific probiotic strains, for example: *L. reuteri* ATCC PTA 6475; *L. paracasei* DSM13434; *L. plantarum* DSM 15312, DSM 15313 and *B. longum*, have the ability to reduce bone loss in ovariectomized rats, but they are applied in the form of live bacteria in the experiments, and it is found that the ability to slow down bone loss is achieved by reducing inflammation. The abovementioned strains do not have the ability to make bone regeneration, and thus the treatments are more passive.

It is therefore necessary to provide a composition for promoting bone regrowth, in order to solve the problems existing in the conventional technology as described above.

SUMMARY OF THE INVENTION

A primary object of the present invention is to provide a composition comprising *Lactobacillus Plantarum* strain GMNL-662 for promoting bone regrowth. The *Lactobacillus Plantarum* strain GMNL-662 can be administrated through any possible pathway in order to enter the digestive system to increase the gene expression of osteogenesis-related cytokine TGF-$\beta$ and osteocalcin, and inhibit the expression of osteoclast related genes (such as TRAP-5), thereby solving the problem caused by bone loss.

To achieve the above objects, the present invention provides a composition for promoting bone regrowth, comprising *Lactobacillus Plantarum* strain GMNL-662 deposited in the China Center for Type Culture Collection (CCTCC) with an accession number of CCTCC M 2016571.

In one embodiment of the present invention, the *Lactobacillus Plantarum* strain GMNL-662 is a viable strain or a dead strain.

In one embodiment of the present invention, the *Lactobacillus Plantarum* strain GMNL-662 has an ability to improve the expression of osteogenic genes.

In one embodiment of the present invention, the osteogenic genes comprise osteocalcin gene.

In one embodiment of the present invention, the composition is a pharmaceutical composition, a nutritional supplement, a health food, a medical food, or the combination thereof.

In one embodiment of the present invention, the composition is applied to slow down bone loss.

DETAILED DESCRIPTION OF THE PREFERRED EMBODIMENTS

Figure 1:
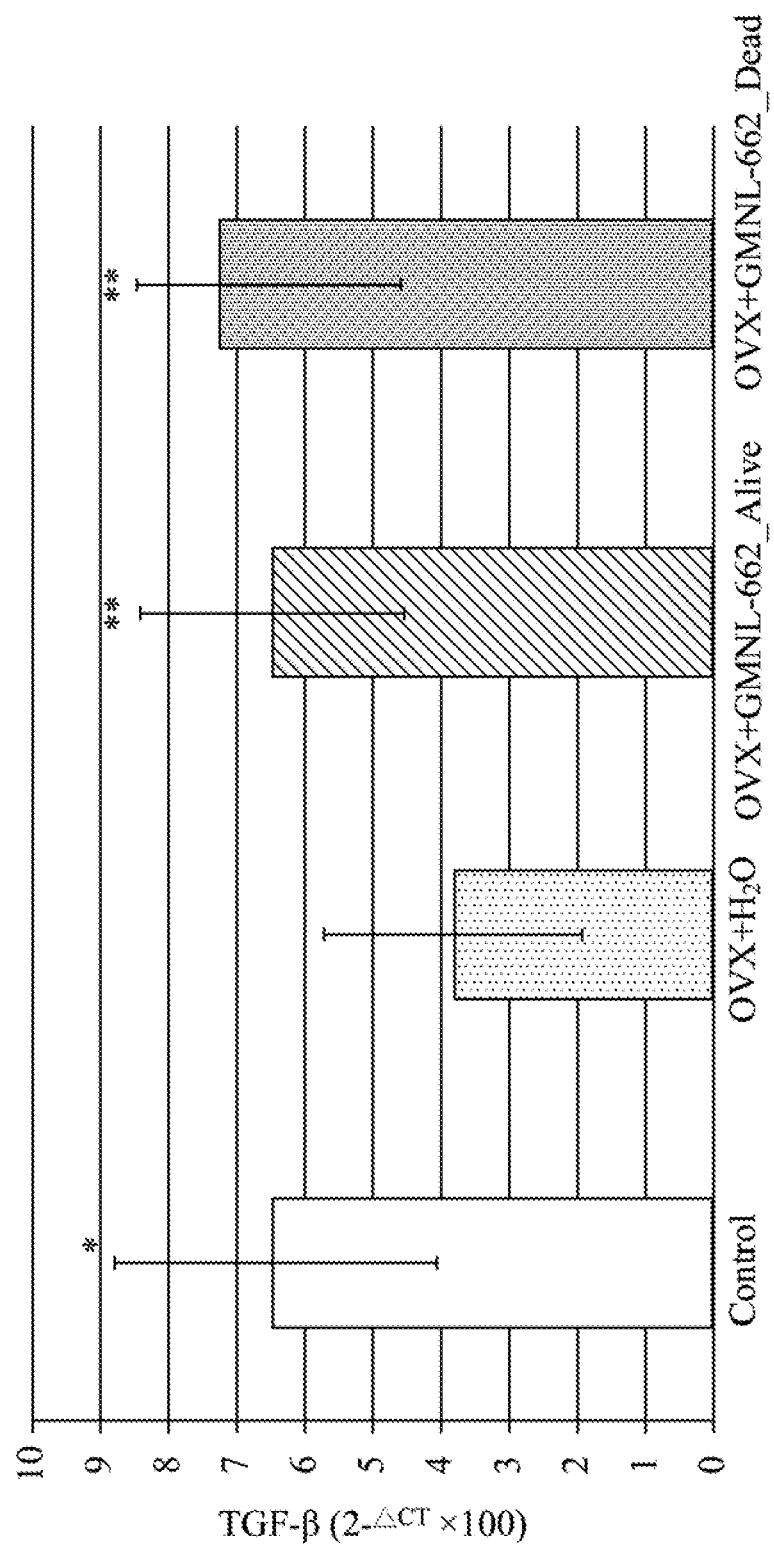
FIG. 1 is a diagram showing the expression of cytokine TGF-$\beta$ of each group in the experiment 2 according to one embodiment of the present invention.

The structure and the technical means adopted by the present invention to achieve the above and other objects can be best understood by referring to the following detailed description of the preferred embodiments. Furthermore, if there is no specific description in the invention, singular terms such as "a", "one", and "the" include the plural number. For example, "a compound" or "at least one compound" may include a plurality of compounds, and the mixtures thereof. If there is no specific description in the invention, "%" means "weight percentage (wt %)", and the numerical range (e.g. 10%-11% of A) contains the upper and lower limit (i.e. 10%≤A≤11%). If the lower limit is not defined in the range (e.g. less than, or below 0.2% of B), it means that the lower limit may be 0 (i.e. 0%≤B≤0.2%). The proportion of "weight percent" of each component can be replaced by the proportion of "weight portion" thereof. The abovementioned terms are used to describe and understand the present invention, but the present invention is not limited thereto.

One embodiment of the present invention provides a *Lactobacillus Plantarum* strain for promoting bone regrowth. The *Lactobacillus Plantarum* strain is referred to as *Lactobacillus Plantarum* strain GMNL-662, which is deposited in the China Center for Type Culture Collection (CCTCC) with an accession number of CCTCC M2016571.

One embodiment of the present invention provides a composition for promoting bone regrowth, comprising the abovementioned *Lactobacillus Plantarum* strain GMNL-662. Preferably, the composition can be a pharmaceutical composition, a nutritional supplement, a health food, a medical food, or the combination thereof. The composition can be formed in various form based on the effectivity or convenience. In addition, the composition is preferably administrated by means of food to enter the digestive system, and can stimulate the expression of osteogenic genes, inhibiting the expression of osteoclast related genes, and promoting the expression of osteogenesis-related cytokine TGF-β to slow down bone loss.

The *Lactobacillus Plantarum* strain GMNL-662 in the abovementioned embodiments is one of a plurality of isolates mainly isolated from human intestines. The primers (SEQ ID NO: 1 and SEQ ID NO: 2) listed in Table 1 are used to perform PCR to reproduce 16S rDNA segments of each isolate, and then sequencing the 16S rDNA segment of each isolate. After sequencing, a 16S rDNA gene sequence of one of the isolates can be obtained as below (SEQ ID NO: 3); subsequently, from the comparison results on the NCBI website, it shows that the 16S rDNA sequences of the isolates are similar to that of the *Lactobacillus Plantarum* strains with identities all over 99%, so that the strain GMNL-662 indeed belongs to the *Lactobacillus Plantarum* genus.

TABLE 1

PCR primer

| Primer | SEQ ID NO: | SEQ |
|---|---|---|
| PAF | 1 | AGA GTT TGA TCC TGG CTC AG |
| 536R | 2 | GTA TTA CCG CGG CTG CTG |

TABLE 2

| NCBI NO | Description | Identity |
|---|---|---|
| KT236093.1 | *Lactobacillus plantarum* KLB 410 | 99% |
| KT962240.1 | *Lactobacillus plantarum* USIM03 | 99% |
| KT025848.1 | *Lactobacillus plantarum* KF | 99% |
| KR816164.1 | *Lactobacillus plantarum* KF9 | 99% |

A complete 16S rDNA sequence (SEQ ID NO: 3) of the *Lactobacillus Plantarum* strain GMNL-662 is listed as below:

GCCGTTGGCGTCGGATACATGCATGTCGTACGAACTCTGG

TATTGATTGGTGCTTGCATCATGATTTACATTTGAGTGAGTGGCGAAC

TGGTGAGTAACACGTGGGAAACCTGCCCAGAAGCGGGGGATAACACCT

GGAAACAGATGCTAATACCGCATAACAACTTGGACCGCATGGTCCGAG

CTTGAAAGATGGCTTCGGCTATCACTTTTGGATGGTCCCGCGGCGTAT

TAGCTAGATGGTGGGGTAACGGCTCACCATGGCAATGATACGTAGCCG

ACCTGAGAGGGTAATCGGCCACATTGGGACTGAGACACGGCCCAAACT

CCTACGGGAGGCAGCAGTAGGGAATCTTCCACAATGACGAAAGTCTGA

TGGAGCAACGCCGCGTGAGTGAAGAAGGGTTTCGGCTCGTAAAACTCT

GTTGTTAAAGAAGAACATATCTGAGAGTAACTGTTCAGGTATTGACGG

TATTTAACCAGAAAGCCACGGCTAACTACGTGCCAGCAGCCGCGGTA

AACAC

A fermentation test to the *Lactobacillus Plantarum* strain GMNL-662 is carried out to obtain the results shown in Table 3.

TABLE 3

Fermentation Test

| Strips No. | carbohydrates substrate | GMNL-662 |
|---|---|---|
| 0 | CONTROL | − |
| 1 | Glycerol | − |
| 2 | Erythritol | − |
| 3 | D-Arabinose | − |
| 4 | L-Arabinose | − |
| 5 | D-Ribose | + |
| 6 | D-Xylose | − |
| 7 | L-Xylose | − |
| 8 | D-Adonitol | − |
| 9 | Methyl-β-D-Xylopyranoside | − |
| 10 | D-Galactose | + |
| 11 | D-Glucose | + |
| 12 | D-Fructose | + |
| 13 | D-Mannose | + |
| 14 | L-Sorbose | − |
| 15 | L-Rhamnose | − |
| 16 | Dulcitol | − |
| 17 | Inositol | − |
| 18 | D-Mannitol | + |
| 19 | D-Sorbitol | + |
| 20 | Methyl-α-D-mannopyranoside | + |
| 21 | Methyl-α-D-glucopyranoside | − |
| 22 | N-Acetyl glucosamine | + |
| 23 | Amygdalin | + |
| 24 | Arbutin | + |
| 25 | Esculin ferric citrate | − |
| 26 | Salicin | + |
| 27 | D-Cellobiose | + |
| 28 | D-Maltose | + |
| 29 | D-Lactose (bovine origin) | + |
| 30 | D-Melibiose | + |
| 31 | D-Saccharose (sucrose) | + |
| 32 | D-Trehalose | + |
| 33 | Inulin | − |
| 34 | D-Melezitose | + |
| 35 | D-Raffinose | − |
| 36 | Amidon (starch) | − |
| 37 | Glycogen | − |
| 38 | Xylitol | − |
| 39 | Gentiobiose | + |
| 40 | D-Turanose | + |
| 41 | D-Lyxose | − |
| 42 | D-Tagatose | − |
| 43 | D-Fucose | − |
| 44 | L-Fucose | − |
| 45 | D-Arabitol | − |

TABLE 3-continued

Fermentation Test

| Strips No. | carbohydrates substrate | GMNL-662 |
|---|---|---|
| 46 | L-Arabitol | − |
| 47 | Potassium gluconate | + |
| 48 | Potassium 2-ketogluconate | − |
| 49 | Potassium 5-ketogluconate | − |

−: negative;
+: positive

To verify the bone regrowth properties of the *Lactobacillus Plantarum* GMNL-662 according to the present invention, and to confirm that the bone loss can be improved, experiments 1 to 3 are executed.

Experiment 1: Bone tissue analysis

Strain: *Lactobacillus plantarum* strain GMNL-662

Strain treatment:

(1) preparation of viable bacteria: Inoculating the *Lactobacillus plantarum* GMNL-662 from a frozen tube to 1 ml of MRS broth, and standing under 37° C. for aerobically incubating for 20 hours. The next day, adding 15 μl culture solution into 1.5 ml of MRS broth (1% secondary activation), and then standing under 37° C. for aerobically incubating for 20 hours. Estimating the bacteria number by using OD 600 to adjust the bacteria concentration to $8 \times 10^7$ CFU/ml.

(2) preparation of dead bacteria: Inoculating the *Lactobacillus Plantarum* strain GMNL-662 from a frozen tube to 1 ml of MRS broth, and standing under 37° C. for aerobically incubating for 20 hours. The next day, adding 15 μl culture solution into 1.5 ml of MRS broth (1% secondary activation), and then standing under 37° C. for aerobically incubating for 20 hours. Estimating the bacteria number by using OD 600 to adjust the bacteria concentration to $4.1 \times 10^8$ CFU/ml.

Osteoporosis mouse model:

8-week-old ICR female rats were purchased from Bio-LASCO Taiwan and ovariectomy was performed when they were 9 week-old. Mice were underwent anesthesia and were ovariectomized through back on both sides of the ovaries. All groups were given the test substance by means of tube feed at 4 days after surgery. The groups were divided into a sham operation group (control group, their abdominal cavity were cut but their ovaries were not removed); and 4 groups ovariectomized group (Ovariectomy; OVX). When the mice were sacrificed, the ovarian tissues were checked and confirmed whether the removal of ovarian was successful. The experimental results of the mice under failure operation were not used. In the 4 groups of the ovariectomized mice, one group was the vehicle group ($H_2O$ group), and one group was the positive drug group (anti-osteoporosis drug Alendronate). Alendronate was formulated with deionized water at a concentration of 0.25 mg/ml. The mice were given 0.1 ml per 10 grams of body weight and 4 times a week. The remaining two groups were fed with 0.2 ml of alive GMNL-662 (strain concentration is $8 \times 10^7$ cfu/ml; daily dose of the mouse is $1.6 \times 10^7$ cfu/mouse, the human dose is $4 \times 10^9$ cfu/60 kg adult), and 0.2 ml of dead GMNL-662 (strain concentration is $4.1 \times 10^8$ cfu/ml; daily dose of the mouse is $8.2 \times 10^7$ cells/mouse, the human dose is $2 \times 10^{10}$ cells/60 kg adult). The two groups were fed with tube one time every day, continued for 28 days, the mice were anesthetized and sacrificed for intraperitoneal cephalic vein sampling, and each femur was removed for analysis.

Analysis method:

The backbone of the right femur far from the end was taken a computer tomography by a micro computed tomography (SkyScan 1076, Kontizh, Belgium, with resolution of 18 μm), and the trabecular bone volume ratio (i.e. bone volume/tissue volume) is analyzed by a software. The analyzed position was selected to include the area of 100 pieces under the growth plate excluding cortical bone. The bone mineral density analysis was applied to the same area. The obtained data in the experiments were analyzed with two-way analysis of variance, and executed T-test statistical analysis. All data were presented as mean ±SD. After comparisons, the abovementioned groups were analyzed statistically and noted by different marks to represent the statistically significant differences (* represents $p<0.05$; ** represents $p<0.01$). See Table 4 and Table 5, showing results of the experiment 1.

TABLE 4

| Trabecular bone volume ratio (BV/TV, bone volume/tissue volume) BV/TV(%) | | | | |
|---|---|---|---|---|
| Control | OVX + $H_2O$ | OVX+ GMNL-662 alive | OVX+ GMNL-662 dead | OVX+ Alendronate |
| 42.12 ± 2.4** | 30.9 ± 1.1 | 36.92 ± 1.7** | 36.8 ± 1.2** | 34.88 ± 0.9** |

From table 4, after removing the ovarian, the trabecular bone volume ratio in (OVX+$H_2O$) group (disease group) was lower than the control group, which means that the osteoporosis animal model was successful. Comparing the alive GMNL-662 group with the dead GMNL-662 group, it can be found that BV/TV thereof were higher than the disease group, which means that the GMNL-662 indeed slows down bone loss in a certain degree after removing the ovarian. Alendronate was positive control group which also had protective effect against bone loss. The two groups of the tube fed GMNL-662 strains even have slightly better protective effects than the anti-osteoporosis drug Alendronate.

TABLE 5

| Femur bone mineral density (BMD, excluding cortical bone) BMD (g/cm³) | | | | |
|---|---|---|---|---|
| Control | OVX + H₂O | OVX+ GMNL-662 Alive | OVX+ GMNL-662 Dead | OVX+ Alendronate |
| 0.502 ± 0.04** | 0.344 ± 0.04 | 0.488 ± 0.02** | 0.474 ± 0.01** | 0.426 ± 0.02* |

From table 5, it can be noted that the disease group (OVX+H$_2$O) has lower BMD than the control group; in the groups of alive and dead GMNL-662 strains, the BMD is significantly higher than the BMD in the disease group (OVX+H$_2$O). That is, both of the two groups of the tube fed GMNL-662 strains can slow down bone loss of the mice after removing the ovarian.

Experiment 2: effects of GMNL-662 on osteogenic genes, cytokines, and osteoclast genes Extraction of tibial RNA: The left femur of the mice were removed, cut into small pieces with scissor, and an appropriate amount of liquid nitrogen was added to grind the bones quickly. The ground bone powder was added to 0.5 ml TRIzol® Reagent to extract RNA; 0.1 ml chloroform was then added thereto to turn up and down 15 times. The solution was placed at room temperature to react for 5 minutes, followed by centrifugalized and extracted the upper layer to new microcentrifuge tubes (eppendorf); 0.25 ml isopropanol was added thereto and the solution was placed at room temperature for 10 minutes and then centrifugalized; the supernatant was removed and the precipitate was washed with 0.5 ml 75% ethanol; after the precipitate was dried, 20-50 µl DEPC water was added to dissolve the precipitate and the RNA concentration was measured.

RNA reverse transcription cDNA: 1-5 µg RNA was obtained and RNase-free water was added therein to 10 µl; additionally, 10×Random primer (2 µl), 10 mM dNTP (1 µl) were added, at 65° C. for 5 minutes, and on ice for 2-3 minutes; after first stage interaction, additional 5×RT buffer (4 µl), 0.1M DTT (1 µl), RNase inhibitor (Invitrogen, RNaseOUTTM, 1 µl), RT enzyme (Invitrogen, SuperScript®III, 1 µl) were added and mixed at room temperature for 5 minutes, and then placed at 50° C. for 60 minutes, at 70° C. for 15 minutes, to proceed the enzyme reverse transcription.

Tibial cDNA in real-time PCR analysis: 1 µl tibial cDNA was obtained and added 4 µl of 1 µM F+R primers (forward/reverse primers are listed below), and 5 µl of 2×Rotor-Gene SYBR Green PCR Master Mix (Qiagen, Cat. 204076), placed into Q-PCR apparatus to react. The relative expression of TGF-β and RANKL were obtained by deducting the GAPDH itself.

TABLE 6

| Primers | | |
|---|---|---|
| TGF-β Forward primer | SEQ ID NO: 4 | GAGTAACGCTTTCCGGAGTC |
| TGF-β Reverse primer | SEQ ID NO: 5 | ACAGTCACCAGCATCTCAGC |
| Osteocalcin Forward primer | SEQ ID NO: 6 | ACGGTATCACTATTTAGGAC CTGTG |
| Osteocalcin Reverse primer | SEQ ID NO: 7 | ACTTTATTTTGGAGCTGCTG TGAC |

TABLE 6-continued

| Primers | | |
|---|---|---|
| TRAP-5 Forward primer | SEQ ID NO: 8 | GACGATGGGCGCTGACTTCA |
| TRAP-5 Reverse primer | SEQ ID NO: 9 | GCGCTTGGAGATCTTAGAGT |
| GAPDH Forward primer | SEQ ID NO: 10 | GCACAGTCAAGGCCGAGAAT |
| GAPDH Reverse primer | SEQ ID NO: 11 | GCCTTCTCCATGGTGGTGAA |

Analysis method: The obtained data in the experiments were analyzed with two-way analysis of variance, and executed T-test statistical analysis. The abovementioned groups were analyzed statistically compared with the OVX+H$_2$O group, wherein * represents $p<0.05$; ** represents $p<0.01$.

As shown in FIG. 1, GMNL-662 alive strain and dead strain both can increase the expression of cytokine TGF-β which can protect bone against bone loss. Comparing the mice of the control group with the disease group (OVX+H$_2$O), the expression of bone regrowth related cytokine TGF-β of the disease group is significantly reduced; the mice fed with GMNL-662 (GMNL-662 alive strain and dead strain) have significant increased expression of TGF-β compared with the disease group (OVX+H$_2$O). This result means that the GMNL-662 strain has ability of promoting the expression of TGF-β so as to slow down bone loss.

Figure 2:
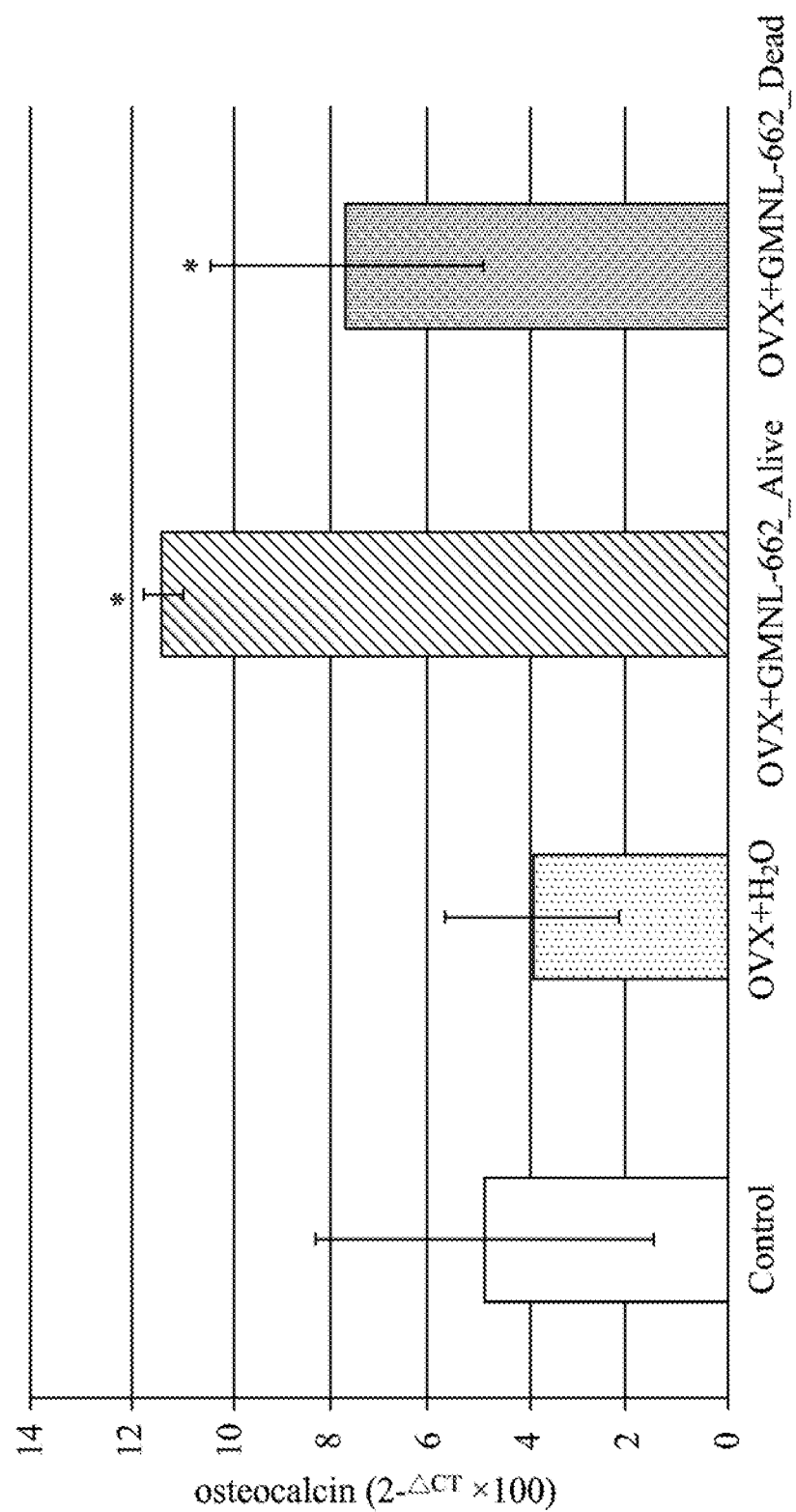
FIG. 2 is a diagram showing the expression of osteogenesis-related gene osteocalcin of each group in the experiment 2 according to one embodiment of the present invention.

Next, as shown in FIG. 2, in the groups of the mice given GMNL-662 (alive or dead strain) after removing ovarian, the expression of osteocalcin gene are higher than the disease group (OVX+H$_2$O), which means that the GMNL-662 strains, no matter the strain is dead or alive, have ability to promote the expression of osteogenic genes, especially osteocalcin gene, thereby slowing down bone loss.

Figure 3:
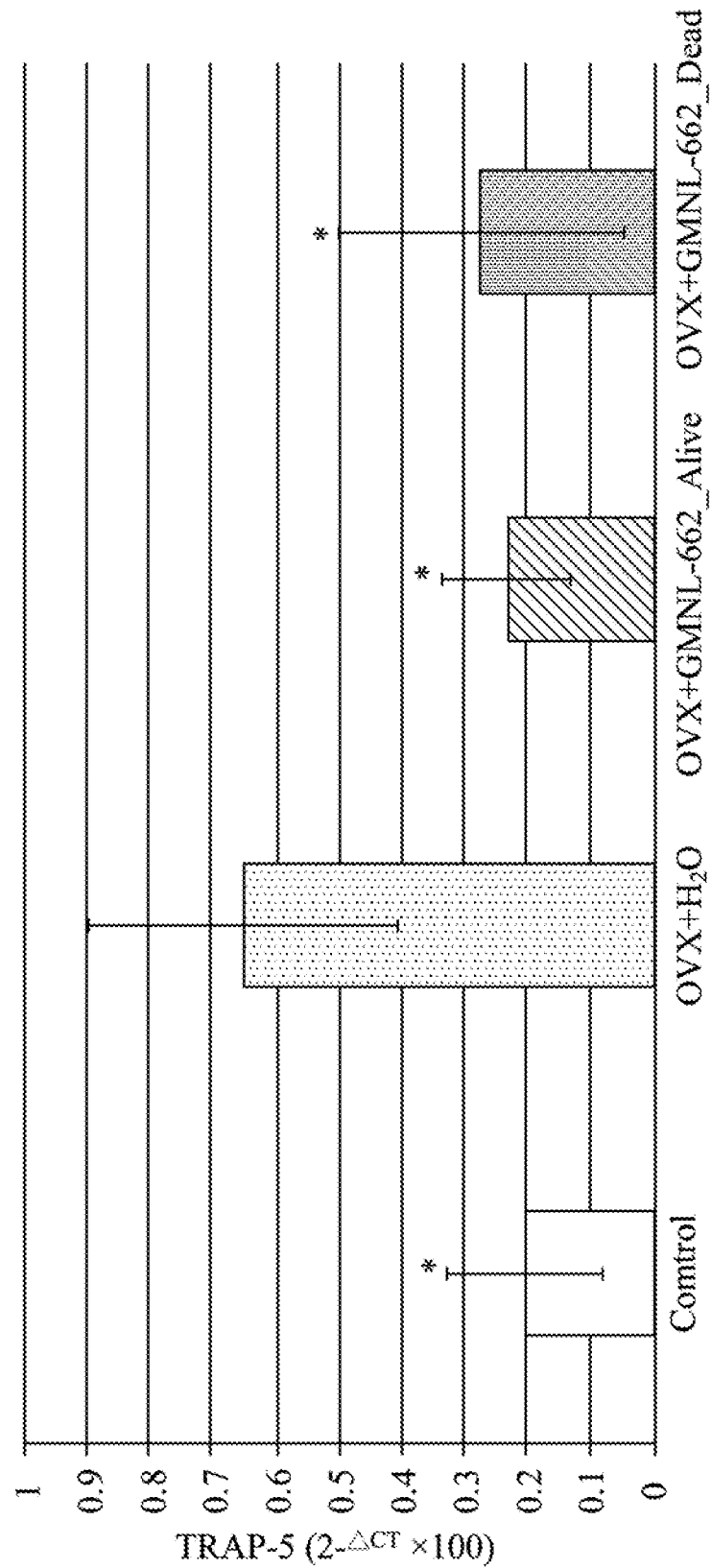
FIG. 3 is a diagram showing the expression of osteoclast related gene TRAP-5 of each group in the experiment 2 according to one embodiment of the present invention.

Refer to FIG. 3, it can be observed apparently, compared with the mice in the sham operation group (Control), the expression of osteoclast related genes TRAP-5 in the disease group (OVX+H$_2$O) is increased; while in the groups of GMNL-662 alive strain and dead strain, the expression of osteoclast related genes TRAP-5 is significantly lower than that in the disease group (OVX+H$_2$O). That is, GMNL-662 strains have ability to inhibit the expression of osteoclast genes so as to slow down bone loss.

In summary, according to the above results, it is certain that the *Lactobacillus Plantarum* strain GMNL-662 according to the present invention, no matter the strains are viable or dead, can significantly slow down bone loss of the mice after removing ovarian in the bone tissue analysis (Trabecular bone volume ratio, BV/TV) of animal experiments and bone mineral density (BMD). It is also noted that the GMNL-662 strain has abilities of promoting the expression of osteogenic genes (Osteocalcin gene), inhibiting the expression of osteoclast related genes (TRAP-5), and promoting the expression of osteogenesis-related cytokine TGF-β, so that the bone loss can be improved. In addition, it can be found in the experiment results that the GMNL-662 has protective effect better than the anti-osteoporosis drug "Alendronate". Alendronate has been found to have many side effects, including heart disease, stubborn pain, jaw osteonecrosis, fractures, and esophageal cancer. Therefore, Lactobacillus Plantarum strain GMNL-662, safe and with no side effects, is applicable to slow down bone loss. It should be a better choice for the menopausal women in considering the future prevention and improvement of bone loss. A deposit designation of a culture of the Lactobacillus plantarum GMNL-662 in the present invention was deposited in the China Center for Type Culture Collection (CCTCC) located at Wuhan University, Wuhan 430072 P.R. China with Accession No. CCTCC M 2016571 on Oct. 17, 2016 under the Budapest Treaty.

The present invention has been described with preferred embodiments thereof and it is understood that many changes and modifications to the described embodiments can be carried out without departing from the scope and the spirit of the invention that is intended to be limited only by the appended claims.

What is claimed is:

1. A method of promoting bone regrowth, comprising: administrating to a subject in need thereof, an effective amount of a composition comprising *Lactobacillus plantarum* GMNL-662 and a pharmaceutically acceptable carrier, wherein the *Lactobacillus plantarum* GMNL-662 is deposited in the China Center for Type Culture Collection (CCTCC) with an accession number of CCTCC M2016571 on Oct. 17, 2016; wherein the *Lactobacillus plantarum* GMNL-662 has an ability to improve expression of osteocalcin gene, an ability to promote expression of cytokine TGF-b, and an ability to inhibit expression of osteoclast gene TRAP-5.

2. The method according to claim 1, wherein the *Lactobacillus plantarum* GMHL-662 is a viable strain.

3. The method according to claim 1, wherein the *Lactobacillus plantarum* GMHL-662 is a dead strain.

4. The method according to claim 1, wherein the composition is a nutritional supplement, food, or a combination thereof.

* * * * *

SEQUENCE LISTING

<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: PAF primer

<400> SEQUENCE: 1
agagtttgat cctggctcag                                                   20

<210> SEQ ID NO 2
<211> LENGTH: 18
<212> TYPE: DNA
<213> ORGANISM: Artificial Sequence
<220> FEATURE:
<223> OTHER INFORMATION: 536R primer

<400> SEQUENCE: 2
gtattaccgc ggctgctg                                                     18

<210> SEQ ID NO 3
<211> LENGTH: 525
<212> TYPE: DNA
<213> ORGANISM: Artificial Sequence
<220> FEATURE:
<223> OTHER INFORMATION: Sequencing Primer

<400> SEQUENCE: 3
gccgttggcg tcggatacat gcatgtcgta cgaactctgg tattgattgg tgcttgcatc       60
atgatttaca tttgagtgag tggcgaactg gtgagtaaca cgtgggaaac ctgcccagaa      120 gcggggata acacctggaa acagatgcta ataccgcata caacttgga ccgcatggtc       180 cgagcttgaa agatggcttc ggctatcact tttggatggt cccgcggcgt attagctaga      240
tggtggggta acggctcacc atggcaatga tacgtagccg acctgagagg gtaatcggcc      300
acattgggac tgagacacgg cccaaactcc tacgggaggc agcagtaggg aatcttccac      360
aatgacgaaa gtctgatgga gcaacgccgc gtgagtgaag aagggtttcg gctcgtaaaa      420
ctctgttgtt aaagaagaac atatctgaga gtaactgttc aggtattgac ggtatttaac      480
cagaaagcca cggctaacta cgtgccagca gccgcgggta aacac                      525

<210> SEQ ID NO 4
<211> LENGTH: 20
<212> TYPE: DNA
<213> ORGANISM: Artificial Sequence
<220> FEATURE:
<223> OTHER INFORMATION: TGF beta Forward primer

```
<400> SEQUENCE: 4
gagtaacgct ttccggagtc                                              20

<210> SEQ ID NO 5
<211> LENGTH: 20
<212> TYPE: DNA
<213> ORGANISM: Artificial Sequence
<220> FEATURE:
<223> OTHER INFORMATION: TGF beta Reverse primer

<400> SEQUENCE: 5
acagtcacca gcatctcagc                                              20

<210> SEQ ID NO 6
<211> LENGTH: 25
<212> TYPE: DNA
<213> ORGANISM: Artificial Sequence
<220> FEATURE:
<223> OTHER INFORMATION: Osteocalcin Forward primer

<400> SEQUENCE: 6
acggtatcac tatttaggac ctgtg                                        25

<210> SEQ ID NO 7
<211> LENGTH: 24
<212> TYPE: DNA
<213> ORGANISM: Artificial Sequence
<220> FEATURE:
<223> OTHER INFORMATION: Osteocalcin Reverse primer

<400> SEQUENCE: 7
actttatttt ggagctgctg tgac                                         24

<210> SEQ ID NO 8
<211> LENGTH: 20
<212> TYPE: DNA
<213> ORGANISM: Artificial Sequence
<220> FEATURE:
<223> OTHER INFORMATION: TRAP-5 Forward primer

<400> SEQUENCE: 8
gacgatgggc gctgacttca                                              20

<210> SEQ ID NO 9
<211> LENGTH: 20
<212> TYPE: DNA
<213> ORGANISM: Artificial Sequence
<220> FEATURE:
<223> OTHER INFORMATION: TRAP-5 Reverse primer

<400> SEQUENCE: 9
gcgcttggag atcttagagt                                              20

<210> SEQ ID NO 10
<211> LENGTH: 20
<212> TYPE: DNA
<213> ORGANISM: Artificial Sequence
<220> FEATURE:
<223> OTHER INFORMATION: GAPDH Forward primer

<400> SEQUENCE: 10
gcacagtcaa ggccgagaat                                              20

<210> SEQ ID NO 11
<211> LENGTH: 20
```

```
<212> TYPE: DNA
<213> ORGANISM: Artificial Sequence
<220> FEATURE:
<223> OTHER INFORMATION: GAPDH Reverse primer

<400> SEQUENCE: 11
gccttctcca tggtggtgaa                                                     20
```